United States Patent [19]
Chatterjee et al.

[11] Patent Number: 5,219,865
[45] Date of Patent: Jun. 15, 1993

[54] PHARMACEUTICAL COMBINATION FOR THE PROPHYLAXIS AND THERAPY OF MALARIA

[75] Inventors: Dipak C. Chatterjee, Bombay; Bindumadhavan Venugopalan, Maharashtra; Bansi Lal; Noel J. de Souza, both of Bombay, all of India; Richard H. Rupp, Königstein/Taunus, Fed. Rep. of Germany

[73] Assignee: Hoechst Aktiengesellschaft, Frankfurt am Main, Fed. Rep. of Germany

[21] Appl. No.: 865,624

[22] Filed: Apr. 9, 1992

Related U.S. Application Data

[63] Continuation of Ser. No. 565,167, Aug. 10, 1990, abandoned, which is a continuation of Ser. No. 191,172, May 6, 1988, abandoned.

[30] Foreign Application Priority Data

May 8, 1987 [DE] Fed. Rep. of Germany ....... 3715378

[51] Int. Cl.$^5$ .................... A61K 31/44; A61K 31/47; A61K 31/335
[52] U.S. Cl. .................................. 514/305; 514/314; 514/450
[58] Field of Search ...................... 514/314, 450, 305

[56] References Cited

U.S. PATENT DOCUMENTS 4,260,615  4/1981  Raether et al. ............. 514/314
4,791,135  12/1988  Lin et al. ................... 514/450

OTHER PUBLICATIONS

Chemical Abstracts 97:16656g (1982).
Chemical Abstracts 108:112772h (1988).
R. Ekong et al., "Synergism Between Arteether And Mefloquine Or Quinine In A Multidrug-resistant Strain Of *Plasmodium Falciparum In Vitro*," Transactions of the Royal Society of Tropical Medicine and Hygiene, 84:757-758 (1990).
A. N. Chawira et al., "The Effect Of Artemisinin Combined With Standard Antimalarials Against Chloroquine-Sensitive And Chloroquine-Resistant Strains of Plasmodium-Falciparum In-vitro," J. Trop. Med. Hyg., 90(1):1-8 (1987) Abstract only.
Y. D. Wan et al., "Study On The Combined Use Of Artemisinine And Primaquine Against Short-Term Malarial Relapse," Yao Hsueh T'ung Pao, 16(1):9-12, 14, (1981) Abstract only.
J. X. Zhang et al., "A Combined Regimen Of Pyronaridin-Artemether-Chloroquine (PAC) For The Treatment Of Plasmodium Cynomoigi In The Rhesus Monkey," Yao Hsueh Hsueh Pao, 19(8):571-575 (Aug. 1984) Abstract only.
G. Li et al., "Randomised Comparative Study Of Mefloquine, Qinghaosu, And Pyrimethamine-Sulfadoxine In Patients With Falciparum Malaria," Lancet (England), 2(8416):1360-1361 (1984) Abstract only.
Tropical Disease Research, Seventh Programme Report, Chapter 2, Malaria, UNDP/WORLD BANK/WHO published by the WHO in 1985 Warhurst, D.C., "Drug Resistance", Pharmaceutical J., Nov. 23 (1985) 689-692.
Nathan, M. B., "A comparison of Mansonella ozzardi microfilaria densities in the blood and in skin snips from three areas of the body", Trans. R. Soc., Trop. Med. and Hyg., 73 (3), 338-340 (1983).

(List continued on next page.)

Primary Examiner—Jerome D. Goldberg
Attorney, Agent, or Firm—Farabow, Garrett & Dunner Finnegan, Henderson

[57] ABSTRACT

The present invention relates to combinations of the malaria therapeutics artemisinine, dihydroartemisinine, arteether, artemether, artesunate or other artemisinine derivatives with one or more of the antimalarials chloroquine, 10-0-methylfloxacrine, quinine, mefloquine, amodiaquine, pyrimethamine, sulfadoxine and primaquine. Synergistic actions are achieved with them on treatment of mammals, including humans, with subcurative doses of the individual substances.

2 Claims, No Drawings

OTHER PUBLICATIONS

Merkli et al., "The Inhibitory Effect of a Drug Combination on the Development of Mefloquine Resistance in Plaasmodium", Annals of Tropical Medicine and Parasitology 74, No. 1: 1–9 (1980).

H. P. Koch, "Qinghaosu: A Potent Antimalarial From Plant Origin", Pharm. Int. 184–185 (1981).

L. J. Bruce-Chwatt, "Qinghaosu: A New Antimalarial", British Med. J. 284: 767–768.

Peters, et al., "The Chemotherapy of Rodent Malaria, XXVII, Studies on Mefloquine", Annals of Tropical Medicine & Parasitology 71, No. 4: 407–418 (1977).

W. Peters, "Prevention of Drug Resistance in Rodent Malaria by the use of Drug Mixtures", Bull W.H.O. 51: 379–383 (1974).

Peters, et al. "Antimalarial Drugs II", Handbook of Experimental Pharmacology 68/11 (1984) Springer Verlag Berlin, Heidelberg, New York, Editors: W. Peters and W. H. G. Richards.

Table of Contents of W.H. O. Report of the Scientific Working Group on the Chemotherapy of Malaria, PDR/Chemal 3rd Review, 85.3 Geneva, Jun. 3–5, 1985.

Raether and Fink, "Antimalarial activity of Floxacrine (HOE 991)I Ann. Trop. Med. and Parasit.", 73, No. 6: 505–526 (1979).

PHARMACEUTICAL COMBINATION FOR THE PROPHYLAXIS AND THERAPY OF MALARIA

This application is a continuation of application Ser. No. 07/565,167, filed Aug. 10, 1990, now abandoned which is a continuation of application Ser. No. 07/191,172, filed May 6, 1988, now abandoned.

The present invention relates to a combination of the malaria therapeutics artemisinine and its derivatives, for example dihydroartemisinine, arteether, artemether or artesunate, with one or more of the antimalarials chloroquine, 10-0-methylfloxacrine, quinine, mefloquine, amodiaquine, pyrimethamine, sulfadoxine, primaquine and the pharmaceutically utilizable salts thereof, for potentiating the action, and to dosage methods for these combinations of active substances.

The generic names used here and elsewhere in the text are taken from "Tropical Diseases Research, Seventh Programme Report", chapter 2; Malaria, UNDP-/WORLD BANK/WHO, published by the WHO in 1985; 10-0-methylfloxacrine is a derivative of the antimalarial floxacrine and has been described in German Patent Application P 36 24 778.2.

Malaria which is resistant to medicaments represents a serious problem for clinical care and public health. The malaria parasite Plasmodium falciparum has developed a versatile ability to elude the action of a medicament by either genetic mechanisms or non-genetic (adaptive) methods. It has been demonstrated that the chloroquine resistance of malaria parasites takes the form of a stable genetically determined property (Warhurst, D. C. Pharmaceut. J. Nov. 23 (1985) 689-692). The spread of Plasmodium falciparum resistant to chloroquine and other antimalarials presents the public health programs in tropical and subtropical countries with a difficult task (Suphat et al., Trans. R. Soc. Trop. Med. and Hyg. (1983) 73 (3), 338-340). The use of combinations of various antimalarials in the chemotherapy of malaria is known. Thus, for example, a combination of amodiaquine and tetracycline and a combination of pyrimethamine and sulfadoxine, which is known under the name Fansidar®, has been used in clinical care (Suphat et al. cit.). More recently, clinical studies have been started on another antimalarial combination, Fansimef (mefloquine, pyrimethamine and sulfadoxine) (WHO loc. cit.).

Peters has reported (Peters et al., Ann. Trop. Med. and Parasit. 71 (1977), 407-418) that the development of resistance can be slowed down in an animal study if one antimalarial is administered in combination with certain other antimalarials. Peters (W. Peters, Bull. W. H.O. 51 (1974), 379-383 and W. Peters, Handbook of Experimental Pharmacology 68/11 (1984) Springer Verlag Berlin, Heidelberg, New York, Editors: W. Peters and W. H. G. Richards) has also drawn attention to the use of appropriate medicament combinations for the treatment of malaria in humans, these not only being able to delay the development of resistance but also improving the success of treatment. Thus, for example, it has been demonstrated that a triple combination of mefloquine, sulfadoxine and pyrimethamine delayed the development of resistance of Plasmodium berghei (Merkli et al., Ann. Trop. Med. and Parasit. (1980), 4 (1), 1-9).

Artemisinine and derivatives have likewise already been disclosed as antimalarials. Artemisinine was isolated from Artemisia annual L., subsequently synthesized and used for the treatment of P. falciparum malaria (H. P. Koch, Pharm. Int. (1981), 184-185; L. J. Bruce-Chwatt, British Med. J. 284 (1982), 767-768). It has also proved to be effective against chloroquine-resistant strains of P. falciparum in humans. Dihydroartemisinine, arteether, artemether and artesunate, for example, are semisynthetic derivatives of artemisinine, and the action thereof against malaria has been described in various reports (W. H. O. Report of the Scientific Working Group on the Chemotherapy of Malaria, PDR/Chemal 3rd Review, 85.3, Geneva, June 3-5, 1985, and references contained therein).

Artemisinine and its derivatives are represented by formula I

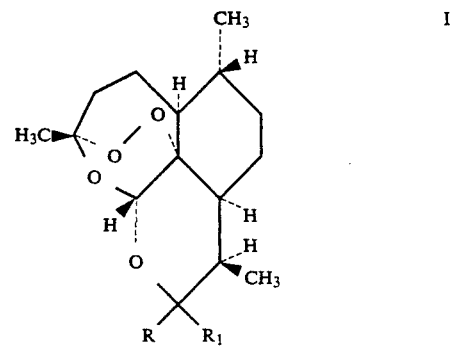

with R and $R_1$ together denoting oxygen (artemisinine), or J R denoting in each case hydrogen, and $R_1$ denoting OH (dihydroartemisinine), —O—$C_1$-$C_6$—alkanoyl, —O—$C_1$-$C_6$—carboxyalkanotyl, —O—cyclo—hexy carbonyl, —O—benzoyl or —O—naphthoyl, as well as the corresponding pharmacologically tolerated salts.

The compound of the formula I with R =H and $R_1$ =—O—$CH_3$ is called artemether, that with R =H and $R_2$ =—O—$C_2H_5$ is called arteether, and that with R =H and $R_1$ =—O—$COCH_2CH_2CO_2Na$ is called artesunate.

It has now been found, surprisingly, that combinations of artemisinine and/or its abovementioned derivatives with the known malaria therapeutics chloroquine, 10-0-methylfloxacrine, quinine, mefloquine, amodiaquine, pyrimethamine, sulfadoxine, primaquine and the pharmaceutically utilizable salts thereof show a synergistic action.

The clinical importance of the present improved compositions for malaria therapy is reflected by relevant animal experiments. The specific examples which follow contain typical test protocols used to examine the ability of the test substance to be an effective antimalarial even for medicament-resistant strains of P. berghei.

The present combination of antimalarials which is described in more detail hereinafter permits the desired malaria treatment, specifically both for prophylaxis and for therapy, and prevents or delays the development of resistance.

Artemisinine or one of its abovementioned derivatives is administered to mammals in general in the range 0.125-10 mg/kg in a single dose each day for 5 days. The other antimalarial which has already been mentioned hereinbefore in this specification (i.e. chloroquine, 10-0methylfloxacrine, quinine, pyrimethamine, mefloquine, amodiaquine, sulfadoxine and primaquine) can be administered separately; in this case, the latter is administered in an amount within the (although usually lower) dose range and in accordance with the treatment regimens (frequency, dosage form and compositions) as are specified for the use thereof in publications to date, for example in the references cited above or further in the said references.

It is advantageous and more convenient to administer artemisinine or one of its derivatives and further antimalarials of the invention in a single combined composition. This can be a form suitable for parenteral administration, but a form suitable for oral administration is to be preferred. The proportion of each medicament in the proposed combined dosage form corresponds to the proportion of the total daily dose of each medicament when it is administered alone. The combined medicaments can be administered in single or divided doses.

In the preferred oral administration, the amount of artemisinine for an average adult patient will in general be in the range 0.2-2 g in combination with 200-400 mg of chloroquine or with 200-400 mg of 10-0-methylfloxacrine as initial dose; the 2nd dose can be administered 6 hours later in the range 0.2-2 g of artemisinine in combination with 100-200 mg of chloroquine or with 100-200 mg of 10-0-methylfloxacrine. The dose administered at the second intake can be maintained for a further 3 days, with a single dose being administered each day.

Combinations of artemisinine or one of its derivatives with other antimalarials of the second group can be administered in a similar manner. In general, a combination of dihydroartemisinine (range 0.2-1.5 g) with chloroquine (range 200-400 mg) or with 10-0-methylfloxacrine (range 200-400 mg) can be administered to an adult patient, with administration 6 hours later of a second dose of 0.2-1.5 g of dihydroartemisinine in combination with 100-200 mg of chloroquine or with 100-200 mg of 10-0-methylfloxacrine. The amount administered as the 2nd dose can in general be administered as a single dose each day for a further 3 days.

It is also possible to administer to an adult patient a combination of arteether (range 0.2-1.5 g) together with chloroquine or with 10-0-methylfloxacrine (range 200-400 mg). The 2nd dose can be administered 6 hours after the 1st dose and can contain 0.2-1.5 g of arteether plus 100-200 mg of chloroquine or 10-0-methylfloxacrine. The amount administered with the 2nd dose can in general be given as a single dose each day for a further 3 days.

The combined substances are administered, both orally and parenterally, alone or in a further combination with pharmaceutically utilizable vehicles. On oral administration, the suitable pharmaceutical vehicles include inert diluents or extenders used for the preparation of tablets, powders, capsules or the like. These pharmaceutical combinations can, if this is desired, contain additional ingredients such as flavorings, binders, corrigents or the like. For example, tablets which contain various corrigents such as sodium citrate, together with various soluble substances such as starch, alginates and certain complex silicates and binders such as polyvinylpyrrolidone, sucrose, gelatin and gum arabic, are used. In addition, lubricants such as magnesium stearate, sodium lauryl sulfate and talc are often suitable for the preparation of tablets. Solid compositions of a similar nature are also used as fillers in filled soft and hard gelatin capsules. Accordingly, the preferred materials include lactose and polyethylene glycols of high molecular weight.

The present invention is illustrated by the examples which follow. However, it ought to be pointed out that the invention is not confined to the specific details of the examples.

EXAMPLE 1

Synergistic therapeutic actions of subcurative doses of artemisinine, dihydroartemisinine and arteether in combination with subcurative doses of chloroquine, 10-0-methylfloxacrine, mefloquine or pyrimethamine against chloroquine-sensitive Plasmodium berghei infection in Swiss mice.

METHODOLOGY OF THE BIOLOGICAL EVALUATION

The assessment of the schizontocidal action in the blood from the "28-day test" described by Raether and Fink (Ann. Trop Med. and Parasit., 73 (1979), 503-526) was used for this.

MICE

All the experiments were carried out with randomly bred male and female Swiss mice which originated from the rearing unit of Hoechst India Limited in Muland, Bombay. The animals were free of Eperythrozoon coccoides. The animals received dry feed and water ad lib. and were housed at a room temperature of 22-25° C.

PARASITE

The London School of Hygiene and Tropical Medicine supplied the strain Plasmodium berghei K-173 which is sensitive to medicaments, and P. berghei (NS) which is moderately resistant to chloroquine. The strains elicit, after they have been inoculated intraperitoneally, a lethal infection with $1 \times 10^7$ parasite-infected erythrocytes per mouse.

ADMINISTRATION OF THE SUBSTANCES

The substances were administered orally or subcutaneously by the methods described by Raether and Fink (loc. cit.). Artemisinine, dihydroartemisinine and arteether were homogenized in doubly refined corn oil and used as suspensions for the subcutaneous inoculation of mice. The medicaments were administered for 5 days. The 1st dose was given within 2 hours after the infection (D+0), followed by D+1, D+2, D+3 and D+4 (intervals of 1 day each).

OBSERVATION OF THE TREATED MICE

From D+4 to D+28 blood smears were prepared at various intervals. The blood smears were obtained from the distal end of the tail and were stained with Giemsa solution. The mice were free of P. berghei on D+28 and were regarded as completely cured. At least 12 mice were investigated for each dose.

The synergistic therapeutic action of subcurative doses of artemisinine, dihydroartemisinine and arteether, each in combination with subcurative doses of chloroquine, mefloquine, pyrimethamine or 10-0-methylfloxacrine, on mice infected with chloroquine-sensitive P. berghei is shown in Table I for oral, and in Table II for subcutaneous,

TABLE I

| Composition | Oral dose (mg/kg × 5) | Mice per group | % infected animals cured |
| --- | --- | --- | --- |
| Chloroquine (curative dose) | 12.5 | 25 | 100 |
| Chloroquine (subcurative dose) | 10 | 27 | 40 |
| 10-O-Methylfloxacrine | 10 | 12 | 100 |

TABLE I-continued

| Composition | Oral dose (mg/kg × 5) | Mice per group | % infected animals cured |
|---|---|---|---|
| (curative dose) | | | |
| 10-O-Methylfloxacrine (subcurative dose) | 5 | 20 | 55 |
| Mefloquine (curative dose) | 7.5 | 20 | 100 |
| Mefloquine (subcurative dose) | 2.5 | 32 | 6 |
| Pyrimethamine (curative dose) | 7.5 | 16 | 100 |
| Pyrimethamine (subcurative dose) | 1.25 | 16 | 18 |
| Artemisinine (curative dose) | 200 | 12 | 100 |
| Artemisinine (subcurative dose) | 100 | 20 | 40 |
| Dihydroartemisinine (curative dose) | 100 | 12 | 100 |
| Dihydroartemisinine (subcurative dose) | 50 | 12 | 50 |
| Arteether (curative dose) | 100 | 12 | 91 |
| Arteether (subcurative dose) | 50 | 15 | 40 |
| Artemisinine + chloroquine | 10 + 10 | 12 | 100 |
| Dihydroartemisinine + chloroquine | 5 + 5 | 12 | 100 |
| Arteether + chloroquine | 7.5 + 5 | 12 | 100 |
| Artemisinine + 10-O-methylfloxacrine | 20 + 5 | 12 | 100 |
| Arteether + 10-O-methylfloxacrine | 10 + 5 | 12 | 100 |
| Dihydroartemisinine + 10-O-methylfloxacrine | 10 + 5 | 12 | 100 |
| Arteether + mefloquine | 10 + 2.5 | 32 | 100 |
| Arteether + pryimethamine | 10 + 1.25 | 21 | 100 |

TABLE II

| Composition | Subcutaneous dose (mg/kg × 5) | Mice per group | % infected animals cured |
|---|---|---|---|
| Chloroquine (curative dose) | 10 | 25 | 100 |
| Chloroquine (subcurative dose) | 5 | 24 | 25 |
| 10-O-Methylfloxacrine (curative dose) | 5 | 19 | 100 |
| 10-O-Methylfloxacrine (subcurative dose) | 2.5 | 13 | 84 |
| Pyrimethamine (curative dose) | 6 | 15 | 100 |
| Pyrimethamine (subcurative dose) | 2.5 | 15 | 66 |
| Artemisinine (curative dose) | 20 | 12 | 100 |
| Artemisinine (subcurative dose) | 1.0 | 12 | 25 |
| Dihydroartemisinine (curative dose) | 4 | 12 | 100 |
| Arteether (curative dose) | 5.0 | 16 | 100 |
| Arteether (subcurative dose) | 1.25 | 16 | 33 |
| Dihydroartemisinine (subcurative dose) | 2 | 12 | 100 |
| Arteether (curative dose) | 5 | 16 | 100 |
| Arteether (subcurative dose) | 1.25 | 16 | 33 |
| Artemisinine + chloroquine | 5 + 5 | 12 | 100 |
| Dihydroartemisinine + chloroquine | 2.5 + 5 | 12 | 100 |
| Arteether + chloroquine | 5 + 5 | 12 | 100 |
| Artemisinine + 10-O-methylfloxacrine | 10 + 2.5 | 12 | 100 |
| Dihydroartemisinine + 10-O-methylfloxacrine | 2.5 + 2.5 | 12 | 100 |
| Arteether + 10-O-methylfloxacrine | 5 + 2.5 | 14 | 100 |
| Arteether + pryimethamine | 1.25 + 1.25 | 22 | 100 |

EXAMPLE 2

Synergistic action of subcurative doses of artemisinine or artemisinine derivatives in combination with subcurative doses of chloroquine, 10-0-methylfloxacrine or pyrimethamine for chloroquine-resistant strains of *Plasmodium berghei* (NS) in infected Swiss mice.

The schizontocidal actions in the blood were assessed by the procedure described in Example 1 using the chloroquine-resistant strains of P. berghei.

The synergistic therapeutic action of subcurative doses of artemisinine, dihydroartemisinine or arteether in combination with subcurative doses of chloroquine or of 10-0-methylfloxacrine or pyrimethamine for infection of Swiss mice with Plasmodium berghei (NS) is shown in Table III for oral and subcutaneous administration. As shown by these data, the mice infected with chloroquine-resistant P. berghei are completely cured with subcurative doses of artemisinine, dihydroartemisinine or arteether in combination with subcurative doses of chloroquine or 10-0-methylfloxacrine or pyrimethamine when the substances are administered either orally or subcutaneously.

TABLE III

| Composition | Route | dose (mg/kg × 5) | Mice per group | % infected animals cured |
|---|---|---|---|---|
| Chloroquine (subcurative dose) | oral | 40 | 24 | 50 |
| | s.c. | 20 | 24 | 50 |
| 10-O-Methylfloxacrine (subcurative dose) | oral | 10 | 17 | 52 |
| | s.c. | 2.5 | 15 | 73 |
| Pyrimethamine (curative dose) | oral | 5.0 | 16 | 100 |
| | s.c. | 1.25 | 20 | 100 |
| Pyrimethamine (subcurative dose) | oral | 0.31 | 40 | 25 |
| | s.c. | 1.25 | 16 | 50 |
| Artemisinine (subcurative dose) | oral | 200 | 12 | 50 |
| | s.c. | 20 | 12 | 50 |
| Dihydroartemisinine (subcurative dose) | oral | 100 | 12 | 50 |
| | s.c. | 5 | 12 | 50 |
| Arteether (subcurative dose) | oral | 100 | 12 | 50 |
| | s.c. | 10 | 15 | 80 |
| Artemisinine + chloroquine | oral | 25 + 15 | 12 | 100 |
| | s.c. | 10 + 15 | 15 | 100 |
| Dihydroartemisinine + chloroquine | oral | 15 + 15 | 12 | 100 |
| | s.c. | 5 + 15 | 15 | 100 |
| Arteether + chloroquine | oral | 10 + 15 | 12 | 100 |
| | s.c. | 5 + 15 | 15 | 100 |
| Artemisinine + 10-O-methylfloxacrine | oral | 15 + 5 | 16 | 100 |
| | s.c. | 10 + 2.5 | 16 | 100 |
| Dihydroartemisinine + 10-O-methylfloxacrine | oral | 15 + 5 | 20 | 100 |
| | s.c. | 2.5 + 2.5 | 16 | 100 |
| Arteether + 10-O-methylfloxacrine | oral | 10 + 7.5 | 14 | 100 |
| | s.c. | 5 + 2.5 | 20 | 100 |
| Arteether + pryimethamine | oral | 20 + 0.31 | 22 | 100 |
| | s.c. | 5 + 0.31 | 22 | 100 |

We claim:

1. A pharmaceutical combination with a synergistic action against malaria, which, besides, customary auxiliaries and vehicles, contains a compound of the formula I

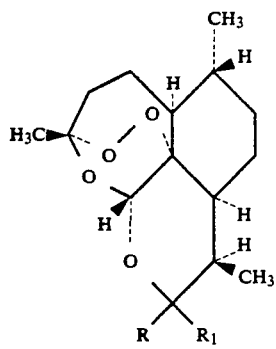

in which R denotes hydrogen, and $R_1$ denotes $-O-C_2H_5$, and pharmacologically tolerated salts thereof and a compound selected from the group consisting of quinine and mefloquine, and the pharmaceutically tolerated salts thereof, said combination in the range of 1:10 to 10:1.

2. A method for the treatment of malaria in a mammal including a human which comprises administering to said mammal an effective amount of the pharmaceutical combination as claimed in claim 1.

* * * * *

UNITED STATES PATENT AND TRADEMARK OFFICE
CERTIFICATE OF CORRECTION

PATENT NO. : 5,219,865
DATED : June 15, 1993
INVENTOR(S) : Dipak Kumar Chatterjee et al It is certified that error appears in the above-indentified patent and that said Letters Patent is hereby corrected as shown below:

On the title page:

Firm name front page, change "Farabow, Garrett & Dunner Finnegan, Henderson" to --Finnegan, Henderson, Farabow, Garrett and Dunner--.

Item [75] Inventors: line 1, change "Dipak C. Chatterjee" to --Dipak K. Chatterjee--.

Signed and Sealed this

Thirteenth Day of September, 1994

Attest:

BRUCE LEHMAN

*Attesting Officer*  *Commissioner of Patents and Trademarks*